United States Patent [19]

Serbousek

[11] Patent Number: 5,098,434
[45] Date of Patent: Mar. 24, 1992

[54] POROUS COATED BONE SCREW

[75] Inventor: Jon Serbousek, Warsaw, Ind.

[73] Assignee: Boehringer Mannheim Corporation, Indianapolis, Ind.

[21] Appl. No.: 619,029

[22] Filed: Nov. 28, 1990

[51] Int. Cl.⁵ .............................................. A61F 5/04
[52] U.S. Cl. ...................................... 606/73; 606/66; 606/76; 623/16
[58] Field of Search ............... 623/18, 13, 16; 606/65, 606/66, 60, 61, 72, 73, 76

[56] References Cited

U.S. PATENT DOCUMENTS

| | | | |
|---|---|---|---|
| 2,414,882 | 1/1947 | Longfellow | 606/73 |
| 3,051,169 | 8/1962 | Grath . | |
| 3,554,193 | 1/1971 | Konstantinou . | |
| 3,605,123 | 9/1971 | Hahn . | |
| 3,808,606 | 5/1974 | Tronzo . | |
| 3,831,213 | 8/1974 | Bedi . | |
| 3,840,904 | 10/1974 | Tronzo . | |
| 3,855,638 | 12/1974 | Pilliar . | |
| 4,177,524 | 12/1979 | Grell et al. . | |
| 4,227,518 | 10/1980 | Aginsky . | |
| 4,476,590 | 10/1984 | Scales et al. . | |
| 4,479,271 | 10/1984 | Bolesky | 623/18 |
| 4,536,894 | 8/1985 | Galante et al. . | |
| 4,537,185 | 8/1985 | Stednitz . | |
| 4,542,539 | 9/1985 | Rowe, Jr. et al. . | |
| 4,546,501 | 10/1985 | Gustilo et al. . | |
| 4,599,085 | 7/1986 | Reiss et al. . | |
| 4,657,460 | 4/1987 | Bein . | |
| 4,681,589 | 7/1987 | Tronzo . | |
| 4,695,282 | 9/1987 | Forte et al. . | |
| 4,711,232 | 12/1987 | Fischer et al. . | |
| 4,743,262 | 5/1988 | Tronzo . | |
| 4,776,329 | 10/1988 | Treharne . | |
| 4,840,632 | 6/1989 | Kampner . | |
| 4,854,496 | 8/1989 | Bugle . | |
| 4,959,064 | 9/1990 | Engelhardt | 606/65 |

FOREIGN PATENT DOCUMENTS 1949923  4/1971  Fed. Rep. of Germany ........ 606/73

Primary Examiner—Robert A. Hafer
Assistant Examiner—David J. Kenealy
Attorney, Agent, or Firm—Perman & Green

[57] ABSTRACT

A bone screw is disclosed for joining bone fragments or for mounting a prosthetic component onto an underlying bone. The bone screw includes a head and an elongated cylindrical shank which is integral with and extends from the head. The shank includes a threaded member and a shoulder member connecting the threaded member and the head, the shoulder member having an outer surface with a porous medium thereon for encouraging bone ingrowth fixation. The outer diameter of the shoulder member is greater than the diameter of a bore of the bone into which the screw is to be threadedly engaged. The head of the screw is provided with a coupling member engageable by a tool for selectively rotating the shank to advance the screw into the bone. As the bone screw is advanced toward a fully seated position, the shoulder member with the porous medium thereon engages the bone in a fitting manner which may be described as a "scratch fit". Initial loosening of the bone screw due to the viscoelastic relaxation of the bone tissue following fixation is thereby largely inhibited and long term loosening of the bone screw is also inhibited by providing an interface onto which or into which bone tissue can grow to stabilize the repair site or the implanted component.

4 Claims, 1 Drawing Sheet

POROUS COATED BONE SCREW

BACKGROUND OF THE INVENTION

1. Field of the Invention

The present invention relates generally to bone fixation screws and, more particularly, to a bone fixation screw of a unique construction designed to inhibit loosening which customarily occurs as the bone relaxes subsequent to fixation.

2. Description of the Prior Art

Currently, bone screws are used to affix bone fragments in direct apposition after proper alignment to promote healing. Upon fracture of a bone, the body's response is to stabilize and heal the fragments in a functional orientation. When a fragment or fragments are displaced in a non-functional or non-anatomical orientation, non-union or malunion can occur. In this instance, open reduction of the fracture may be necessary.

In open reduction, a surgical opening is made, the fracture fragments are realigned, and plates and screws, wire, or other hardware are added to secure the fracture fragments to the bones from whence they came. When a screw is used, whether to secure two fragments together or to secure a plate to the bone, and the screw is tightened, initially, tension in the screw is very high, and holds the fragments together. However, bone is a viscoelastic material and undergoes a phenomenon known as stress relaxation immediately after torque has been applied to the screw. The stress relaxation response is quite pronounced and causes immediate and rapid reduction in the screw tension and, hence, the force holding the fragments together. Typical constructions of known orthopedic fasteners are disclosed in U.S. Pat. No. 4,537,185 to Stednitz, U.S. Pat. No. 4,711,232 to Fisher et al, U.S. Pat. No. 4,227,518 to Aginsky, U.S. Pat. No. 3,554,193 to Constantinou, and U.S. Pat. No. 3,051,169 to Grath. In each of these instances, a standard rigid screw is employed which is certain to become loosened relatively rapidly due to the stress relaxation phenomenon previously mentioned.

Of course, the same situation exists when adjoining bone fragments resulting from a fracture are re-joined before the healing process has begun. Bone screws may also be used to provide allograft or auto-graft fixation during revision surgery or to provide secondary fixation of an orthopedic component, such as an acetabular cup, tibial tray, glenoid component, ulnar component, or the like, to the prepared bony structure at the time of total joint replacement surgery. Bone screws may also be used to fix bone fragments in a traumatic case in which screw removal may be unlikely. In each of these events, however, while the screws provide an initial fixation, the viscoelastic material properties of bone will not maintain the compressive loads generated by the screws. As a result, within a relatively short time, the initial fixation may be greatly compromised.

SUMMARY OF THE INVENTION

It was with knowledge of the mentioned shortcomings of conventional constructions that the present invention has been devised with the result that viscoelastic loosening of bone screws which has heretofore been a persistent problem is now drastically reduced. The invention relates to a bone screw for joining bone fragments or for mounting a prosthetic component onto an underlying bone. The bone screw includes a head and an elongated cylindrical shank which is integral with and extends from the head. The shank includes a threaded member and a shoulder member connecting the threaded member and the head, the shoulder member having an outer surface with a porous medium thereon for encouraging bone ingrowth fixation. The outer diameter of the shoulder member is greater than the diameter of a bore of the bone into which the screw is to be threadedly engaged. The head of the screw is provided with a coupling member engageable by a tool for selectively rotating the shank to advance the screw into the bone. For example, heads are available in hex, torque, Phillips, slots, and other commonly used shapes for engagement by an appropriate tool.

The screws would also have the customary cancellous and cortical thread patterns in lengths from approximately 5 mm for small fragment applications to 75 mm and greater for other purposes. They may also be available in various shoulder and thread lengths and in various ratios of shoulder to thread lengths. Also, the screws of the invention would be available in a wide variety of diameters as well as being fabricated from the common biocompatible orthopedic materials including titanium, cobalt chromium, stainless steel, and the alloys of those metals as well as appropriate composite materials.

In a typical procedure, the underlying bone which is nearest the head of the bone screw when the bone screw has attained its final, or tightened, position, is bored to a diameter which is similar to or slightly less than the outer diameter of the threads on the screw. As a result, there is an interference fit between the bore and the shoulder member of the bone screw. With this construction, as the bone screw is advanced toward a tightened position, the outer surface of the shoulder member having the porous medium thereon engages the bone in a fitting manner which may be described as a "scratch fit". This construction inhibits initial loosening of the bone screw due to the viscoelastic relaxation of the bone tissue immediately following fixation. Furthermore, long term loosening of the bone screw is also inhibited by providing an interface onto which or into which bone tissue can grow to stabilize the repair site or the implanted component.

Applications for such a fastener include, but are not to be limited to, re-joining fractured bone fragments, allograft or auto-graft fixation, for compression hip screws, for cortical screws used with plates for long bone fractures, for cancellous fixation of proximal tibia fractures, and for repair of distal condylar femoral fractures as well as screws for securing total joint arthroplasty components such as, but not limited to, acetabular cups, tibial trays, glenoid components, and ulnar components.

Other and further features, objects, advantages, and benefits of the invention will become apparent from the following description taken in conjunction with the following drawings. It should be understood that the foregoing general description and the following detailed description are exemplary and explanatory but are not intended to be restrictive of the invention. The accompanying drawings which are incorporated in and constitute a part of the invention, illustrate one of the embodiments of the invention and, together with the description, serve to explain the principles of the invention in general terms. Like numerals refer to like parts throughout the disclosure.

DETAILED DESCRIPTION OF THE PREFERRED EMBODIMENT

Figure 1:
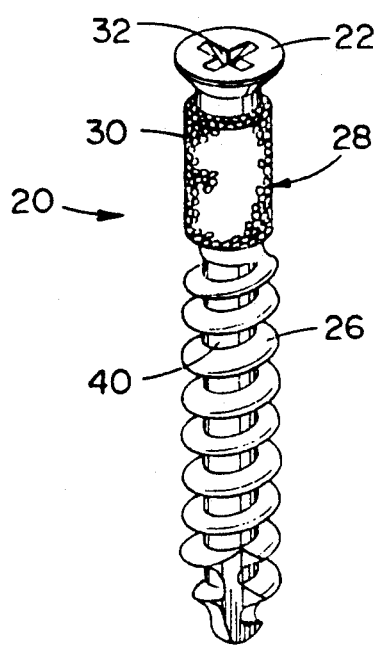
FIG. 1 is a perspective view of a porous coated bone screw embodying the invention.
Figure 2:
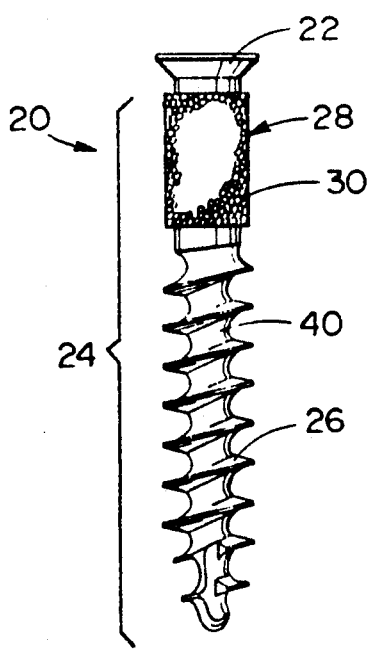
FIG. 2 is a side elevation view depicting the bone screw illustrated in FIG. 1.

Turn now to the drawings, and initially, to FIGS. 1 and 2 which are illustrative of the bone screw 20 of the invention. The bone screw 20 includes a head 22 and a shank 24 which is integral with the head and extends away from the head. The shank 24 includes a threaded member 26 and a shoulder member 28 which connects the threaded member and the head. The shoulder member 28 has an outer surface 30 provided with a porous medium thereon which encourages bone ingrowth fixation. The porous medium on the outer surface 30 may be, for example, the proprietary coating of DePuy division of Boehringer Mannheim Corporation provided under the trademark "POROCOAT", as suitably bonded thereon.

The bone screw 20 is composed of any suitable biocompatible material to which a porous medium such as the "POROCOAT" coating could be applied. Thus, the bone screw 20 could be fabricated of titanium, cobalt chromium, stainless steel, and alloys of all of those metals, as well as appropriate composite materials. The head 22 is illustrated in FIG. 1 as being provided with a coupling mechanism in the form of a cross-shaped slot 32 sized and shaped for mating reception by the terminal portion of a Phillips head screw driver (not shown). So engaged with the bone screw 20, the screw driver can selectively rotate the shank 24 about its longitudinal axis to enable the threaded member 26 to engage the bone and advance the screw 20 toward a seated position. Although the cross shaped slot 32 has been illustrated for reception of the terminal portion of a Phillips head screw driver, it will be appreciated that various other formations can be utilized to obtain a similar result. Thus, hexagonal shaped bores may be provided to receive an appropriately sized Allen wrench, or the head 22 may be slotted to receive a conventional blade-type screw driver, or a star-shaped slot may be provided in the head 22 to receive the terminal portion of an associated torque applying tool. Still other shapes and styles of coupling mechanisms can be envisioned.

Figure 3:
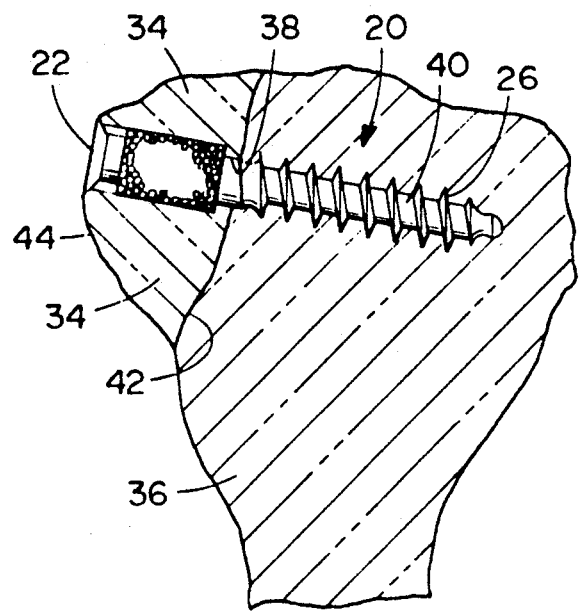
FIG. 3 is a cross section view illustrating the bone screw of the invention joining two bone fragments.

FIG. 3 is illustrative of one typical use for the bone screw 20 of the invention. In this example, it is desired to join a bone fragment 34 to a mating bone fragment 36. In this situation, the bone fragment 34 is first formed with a bore 38 which is substantially larger than the solid core portion 40 of the shank 24 while being somewhat smaller than or equal to the outer diameter of the shoulder member 28.

Figure 4:
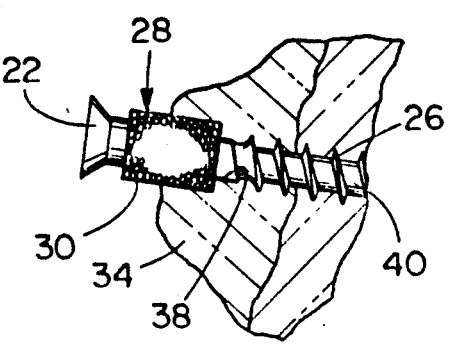
FIG. 4 is a detail cross section view of a bone fragment threadedly receiving the bone screw of the invention, with the bone screw being depicted as being only part way toward a seated position.

When it comes time to join the bone fragments 34 and 36, they are placed in a contiguous relationship along a line of fracture 42 and the bone screw 20 is advanced through the bore 38 by operation of a suitable tool in the customary fashion. As seen in FIG. 4, the threaded member 26 threadedly advances through the bore 38 and into the bone fragment 36. In time, the shoulder member 28 moves toward, then into engagement with, the bore. It will be appreciated that the diameter of the outer surface 30 of the shoulder member 28 is selected to insure an optimal "scratch fit" while not being so great as to cause the bone fragment 34 to fracture further. Both the length of the shoulder member 28 and its diameter are chosen to result in an optimal fixation of the bone screw 20 with the underlying bone. The bone screw 20 continues to advance until the head 22 is substantially flush with an outer surface 44 of the bone fragment 36. In this manner, the head 22 will not cause irritation with soft tissue surrounding the site of the fixation.

When this stage is reached, the bone fragments 34 and 36 are drawn, and held, together in a contiguous engagement. Initial loosening of the bone screw which was commonplace when using conventional bone screws due to the viscoelastic relaxation of the bone tissue is thereby inhibited because of the inability of the bone fragment 34 to move relative to the shank 24. Thereafter, long term loosening of the bone screw is avoided by reason of the porous outer surface 30 which provides an interface onto or into which bone tissue can grow to further stabilize and securely hold the bone screw in position.

Figure 5:
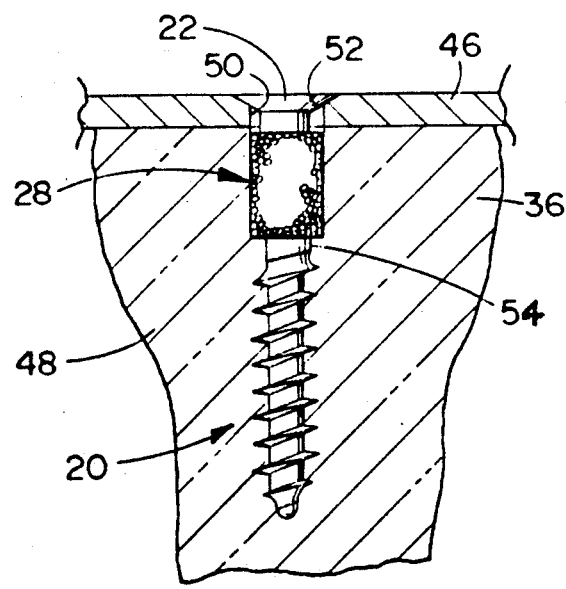
FIG. 5 is a cross section view illustrating the bone screw of the invention fixing a prosthetic component to an underlying bone.

Another suggested use for the bone screw 20 is illustrated in FIG. 5. In FIG. 5, a prosthetic component 46 is depicted as being affixed to an underlying bone 48 by means of the bone screw 20. The prosthetic component 46 may be of any type and at any location of the body. Typical forms of the prosthetic component 46 may be an acetabular cup, a tibial tray, a glenoid component, or an ulnar component. However, these are merely representative of the types of prosthetic components and are not intended to be limiting of the invention. As seen in FIG. 5, the prosthetic component 46 has at least one mounting hole 50 extending completely therethrough and may further be provided with a seat 52 for mating reception with the head 22 of the bone screw 20. As in the instance of the bone fragment 34, the bone 48 is pre-drilled to form an initial bore 54 which is somewhat smaller in diameter than the outer diameter of the shoulder member 28. As explained previously with respect to FIGS. 3 and 4, the bone screw 20 is advanced until the shoulder member 28 engages the drilled bore 54 in the bone 48 and, with continued advancement of the bone screw 20, the shoulder member fittingly engages the bone and continues to do so until the head 22 is fully engaged with the seat 52 on the prosthetic component 46.

Once again, when this occurs, the prosthetic component 46 is firmly affixed to the bone 48. There will be only minimal loosening of the bone screw 20 relative to the bone 48 resulting from the viscoelastic relaxation of the bone tissue. Similarly, long term loosening of the bone screw and, therefore, of the prosthetic component 46 is avoided by the provision of the porous outer surface 30 onto which or into which bone tissue can grow to permanently stabilize the prosthetic component 46.

While preferred embodiments of the invention have been disclosed in detail, it should be understood by those skilled in the art that various other modifications may be made to the illustrated embodiments without departing from the scope of the invention as described in the specification and defined in the appended claims.

I claim:

1. A bone screw for joining a first bone fragment having a throughbore to a second bone fragment comprising:
    a head including coupling means engageable by a tool for rotating said bone screw about a longitudinal axis;
    an elongated cylindrical shank integral with and extending from said head, said shank including a threaded member for threaded engagement with the second bone fragment and a shoulder member connecting said threaded member and said head;
    a porous metallic medium exclusively on said shoulder member for bone ingrowth fixation, said porous medium defining a rough outer peripheral surface;
    said shoulder member adapted for fitting reception into the throughbore of the first bone such that said outer peripheral surface engages the first bone in a scratch fit as selective rotation of said shank by the tool in an advancing direction draws said head into engagement with the first bone fragment and draws the first and second bone fragments into contiguous engagement;
    whereby viscoelastic relaxation of tissue in the first and second bone fragments is inhibited in the region of said porous medium for initial fixation of said bone screw relative to the first and second bone fragments while bone ingrowth into said porous medium is occurring for permanent fixation of said bone screw to the first and second bone fragments.

2. A screw for attaching a prosthetic member to an underlying bone having a bore therein, said screw comprising:
    a head including coupling means engageable by a tool for rotating said screw about a longitudinal axis;
    an elongated cylindrical shank receivable through a mounting hole in the prosthetic member, said shank being integral with and extending from said head, said shank including a threaded member for threaded engagement with the underlying bone and a shoulder member connecting said threaded member and said head;
    a porous metallic medium exclusively on said shoulder member for bone ingrowth fixation, said porous medium defining a rough outer peripheral surface;
    said shoulder member adapted for fitting reception into the bore of the underlying bone such that said outer peripheral surface engages the first bone in a scratch fit as selective rotation of said shank by the tool in an advancing direction draws said head into engagement with the prosthetic member and draws the prosthetic member into contiguous engagement with the bone;
    whereby viscoelastic relaxation of tissue in the bone is inhibited in the region of said porous medium for initial fixation of said screw relative to the bone while bone ingrowth into said porous medium is occurring for permanent fixation of said bone screw to the bone.

3. In combination:
    a prosthetic component adapted to be mounted to a bone having a bore therein, said prosthetic component having at least one mounting hole therethrough;
    a bone screw for fixing said prosthetic component to the bone including:
    a head adapted for engagement with said prosthetic component and including coupling means engageable by a tool for rotating said screw about a longitudinal axis;
    an elongated cylindrical shank receivable through the mounting hole in said prosthetic component, said shank being integral with and extending from said head, said shank including a threaded member for threaded engagement with the bone and a shoulder member connecting said threaded member and said head;
    a porous metallic medium exclusively on said shoulder member for bone ingrowth fixation, said porous medium defining a rough outer peripheral surface;
    said shoulder member adapted for fitting reception into the bore of the bone such that said outer peripheral surface engages the bone in a scratch fit as selective rotation of said shank by the tool in an advancing direction draws said head into engagement with said prosthetic component and draws said prosthetic component into contiguous engagement with the bone;
    whereby viscoelastic relaxation of tissue in the bone is inhibited in the region of said porous medium for initial fixation of said screw relative to the bone while bone ingrowth into said porous medium is occurring for permanent fixation of said bone screw to the bone.

4. A bone screw as set forth in claim 1 composed of a material selected from the group consisting of titanium and alloys thereof, cobalt chromium and alloys thereof, stainless steel and alloys thereof, and composite materials.

* * * * *